United States Patent [19]

Buchholz et al.

[11] 4,302,605

[45] Nov. 24, 1981

[54] PROCESS FOR THE MANUFACTURE OF DIMETHYL SULFIDE

[75] Inventors: Bernard Buchholz, Whitpain; Edward J. Dzierza, Philadelphia, both of Pa.

[73] Assignee: Pennwalt Corporation, Philadelphia, Pa.

[21] Appl. No.: 141,707

[22] Filed: Apr. 18, 1980

[51] Int. Cl.³ ............................................. C07C 149/10
[52] U.S. Cl. ......................................... 568/60; 568/59; 568/71
[58] Field of Search ............................. 568/59, 60, 71

[56] References Cited

U.S. PATENT DOCUMENTS

| | | | |
|---|---|---|---|
| 2,816,146 | 12/1957 | Doumani | 568/60 |
| 2,820,831 | 1/1958 | Doumani | 568/71 |
| 2,829,171 | 4/1958 | Doumani | 568/71 |
| 2,950,323 | 8/1960 | Loev et al. | 568/71 |
| 3,006,966 | 10/1961 | Doumani | 568/71 |
| 3,053,902 | 9/1962 | Doumani | 568/71 |
| 3,662,002 | 5/1972 | Magerlein et al. | 568/60 |

*Primary Examiner*—Donald G. Daus
*Assistant Examiner*—M. C. Eakin

[57] ABSTRACT

A process is provided for preparing dialkyl sulfides by reacting alkanols and hydrogen sulfide in the presence of a zeolite catalyst that contains a reduced amount of alkali metal cations.

16 Claims, 1 Drawing Figure

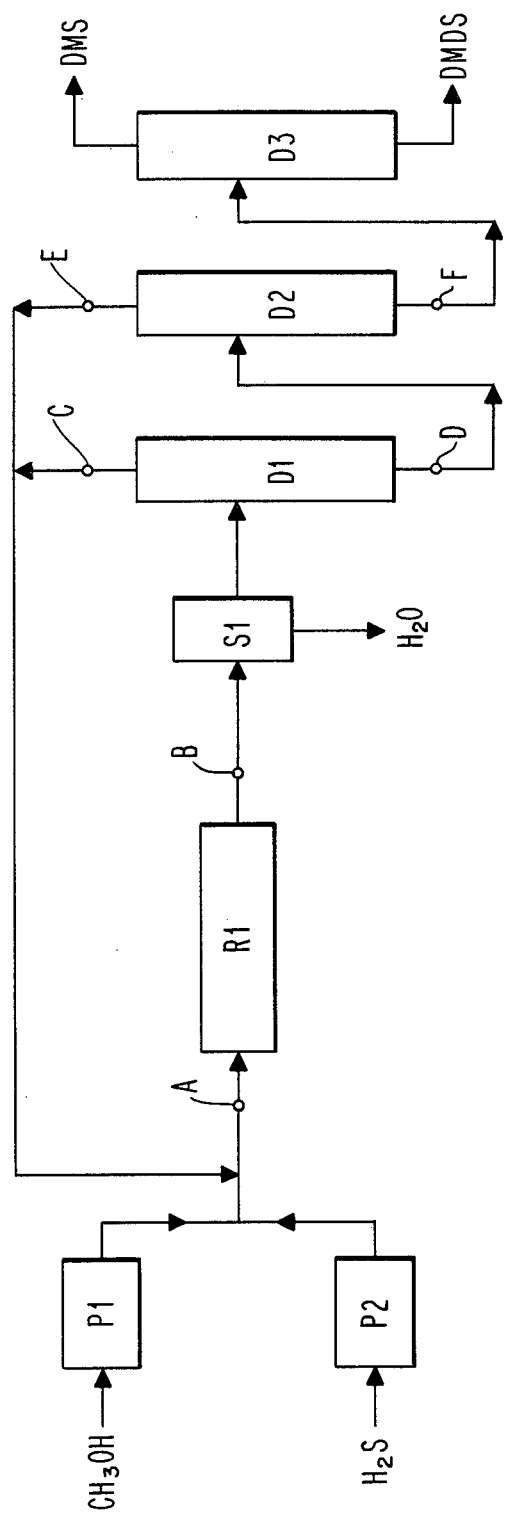

PROCESS FOR THE MANUFACTURE OF DIMETHYL SULFIDE

BACKGROUND OF THE INVENTION

This invention relates to a continuous vaporphase process for the manufacture of dialkyl sulfides by reacting alkanols and hydrogen sulfide in the presence of zeolite catalysts. More particularly, it relates to a process for the continuous manufacture of dimethyl sulfide (DMS) from methanol and hydrogen sulfide in the presence of a solid zeolite catalyst having a reduced alkali metal content.

DMS is a well known article of commerce, being used as a gas odorant, as a sulfiding agent for the post-regeneration treatment of hydrodesulfurization catalysts in petroleum refining, and as an intermediate for the manufacture of the specialty solvent dimethyl sulfoxide. In the past, the commercial requirements for DMS have been largely met by extraction from "black liquor" in wood pulp and paper operations and as a by-product from the manufacture of methyl mercaptan. Recently, however, the markets for DMS have outstripped its availability from these conventional sources, and there is now a need to manufacture additional quantities by independent means. The process of this invention provides an efficient method for producing DMS commercially.

It has been known for some time that DMS is produced as a by-product when methanol and hydrogen sulfide are reacted over dehydrating catalysts such as thoria, zirconia, and alumina to make methyl mercaptan. [E. E. Reid, *Organic Chemistry of Bivalent Sulfur*, Volume 1, p. 38 (1958), Chemical Publishing Co., Inc., New York]. Past research efforts in this area have centered on the development of more selective catalysts to favor the formation of methyl mercaptan over dimethyl sulfate, since supplies of the latter as a by-product from methyl mercaptan manufacture and pulp and paper operations exceeded its market demand. Examples of such mercaptan-selective catalysts are alumina promoted with alkali metal tungstates (U.S. Pat. No. 2,786,079 and U.S. Pat. No. 2,820,062) and with heteropolyacids and their alkali metal salts (U.S. Pat. No. 3,035,097).

STATEMENT OF THE INVENTION

This invention is directed to a continuous vapor-phase process for preparing $C_1$ to $C_{12}$ dialkyl sulfide that comprises reacting a $C_1$ to $C_{12}$ alkanol with hydrogen sulfide in the presence of a zeolite catalyst at elevated temperatures, said zeolite catalyst being Type X, Type Y, or Type L, and containing less than 10% by weight of an alkali metal, expressed as $Na_2O$.

DEFINITIONS

A class of catalysts has been found that possesses an improved selectivity for the formation of sulfides over mercaptans. Further, a continuous process has been found in which these sulfide-selective catalysts are used to provide an economical method for the manufacture of dialkyl sulfides, particularly DMS, on a commercial scale.

Excellent results are obtained in the reaction of hydrogen sulfide ($H_2S$) with alkyl alcohols, ROH, where R is a primary, secondary, or tertiary alkyl group, containing from 1 to 12 carbons, to produce the corresponding dialkyl sulfides ($R_2S$), when said reaction is carried out in the presence of a synthetic zeolite catalyst having an alkali metal content (expressed as $Na_2O$) of less than 10% by weight.

The synthetic zeolite (molecular sieve) catalysts are synthetic aluminosilicates characterized by high uniformity, well-defined pore size, large surface area, complete crystallinity and excellent reproducibility. Their structures are described in the Union Carbide booklet F-08 entitled, "Linde Molecular Sieve Catalysts," and D. W. Breck's textbook, "Zeolite Molecular Sieves," John Wiley & Sons (1974). Various types are currently marketed by Linde (Union Carbide), Houdry (Air Products and Chemicals), Davison (W. R. Grace), Norton, and Akzo (Akzonia).

The basic structural units of synthetic zeolites are Si and Al atoms tetrahedrally coordinated with four oxygen atoms. The oxygen atoms are mutually shared between tetrahedral units contributing one of the two valence charges of each oxygen atom to each tetrahedron. Since aluminum atoms are trivalent, each $AlO_4^{3-}$ is negatively charged. The charge on these units is balanced by cations, generally $Na+$ or $K+$, in the as-synthesized zeolites. These cations are exchangeable with other cations. For example, a divalent cation such as cobalt or nickelous nickel will replace 2 univalent cations; a trivalent cation such as chromium, lanthanum, or cerium will replace 3 univalent cations; and a tetravalent cation such as thorium will replace 4 univalent cations. It is thus possible to replace the alkali metal cations $Na+$ or $K+$ with catalytically more active cations such as $Ni+2$, $CO+2$, $Fe+2$, or $+3$, $Mo+2$ or $+3$, $Cr+3$, $La+3$, $Th+4$, etc., if desired.

Although many factors influence the catalytic activity of these zeolites, the three most important are:
1. The open framwork structure with its attendant pore size.
2. The $SiO_2:Al_2O_3$ ratio of the framework.
3. The cations.

As in most commercial catalytic conversion processes, however, only the large-pore zeolites having pore openings in the range of 7 to 10 Angstroms are useful. The two most preferred are Type X and Type Y zeolites. The Type L, more siliceous than Type X and Type Y, also has a pore size in this range. Types X, Y, and L are distinct, commercially available compositions, well known to those skilled in the art of zeolite chemistry. Type X has a chemical composition expressed in terms of oxide ratios of $Na_2O:Al_2O_3:2-3$ $SiO_2$ with a typical unit cell composition in the hydrated state of $Na_{86}[(AlO_2)_{86}(SiO_2)_{106}].264\ H_2O$. Type Y, on the other hand, has a composition of $Na_2O:Al_2O_3:>3-6$ $SiO_2$. When the $SiO_2:Al_2O_3$ molar ratio is 4.8, the hydrated unit cell composition is $Na_{56}[(AlO_2)_{56}(SiO_2)_{136}].264\ H_2O$. Both of these zeolites crystallize in the cubic system.

An important building block of these zeolites is the sodalite cage, a truncated octahedron unit consisting of 24 (Si, $AlO_4$) units. In Type X and Type Y the sodalite cages are connected through 4 of the 8 hexagonal faces in a tetrahedral arrangement. The pores thus created are defined by a 12-member ring of oxygen atoms, approximately 7–9 A in size, opening into a central cavity of about 11 A in diameter.

The preferred synthetic zeolites are types X and Y because of their larger pore sizes. The ability of the Y type to withstand higher temperatures without losing its crystalline structure makes it the most preferred zeolite catalyst for this invention.

The zeolites, as prepared, generally contain as the cation about 13 percent by weight sodium (as $Na_2O$) or equivalent amount of other alkali metal. As explained above, this cation may be replaced with other cations to reduce the sodium content. In this invention the zeolite catalyst contains less than 10 percent alkali metal (expressed as $Na_2O$), preferably less than 5 percent and more preferably less than 3.0 percent by weight.

An example of the process in which this catalyst is used to advantage is depicted in FLOW DIAGRAM 1 for the manufacture of DMS. Methanol and $H_2S$ are fed continuously in a molar ratio of about 2 to 1, according to the stoichiometric requirement of the equation $2CH_3OH + H_2S \rightarrow CH_3SCH_3 + 2H_2O$. The reactants are vaporized in preheaters (P1 and P2), mixed, and passed into the reactor (R1) containing the zeolite catalyst. Elevated temperatures, in the range of 250°–450° C., and pressures from atmospheric to 600 psig are used to effect reaction. The crude product (B) is cooled and passed into a water-separator (Sl) where by-product water is removed. From there the crude product is passed into a series of continuous distillation towers (or columns). The first tower (or column) (D1) removes the low-boilers (unreacted $H_2S$ and methane, carbon dioxide, nitrogen, or other inert gases that are used for heat removal in the process) in the overhead stream (C) and recycles them back to the reactor (R1). About 5 to 30 moles of an inert gas or mixture of gases, such as nitrogen, methane, or carbon dioxide, are needed per mole of methanol, to remove heat from the reactor for this exothermic reaction.

The bottoms stream (D) is then passed to the second distillation tower (or column) (D2) where unreacted methanol and the intermediate methyl mercaptan, from the reaction $CH_3OH + H_2S \rightarrow CH_3SH + H_2O$, are removed in the overhead stream (E) and recycled, along with stream C, to the reactor (R1). On recycling, the intermediate methyl mercaptan is converted to DMS, according to the equation $2CH_3SH \rightarrow CH_3SCH_3 + H_2S$, over the zeolite catalyst. The latter is a well known reaction, having been recognized, for example, in U.S. Pat. No. 2,667,515. It is the particular advantage of the zeolite catalysts of this invention, that they are exceptionally efficient, much more so than the conventional dehydration catalysts, for converting the recycled intermediate methyl mercaptan to DMS according to the above equation. The intermediate methyl mercaptan is generally totally recycled in this process to produce DMS from methanol and $H_2S$ in high overall yield, although some of it can be separated and collected as a by-product, if so desired.

The bottoms-stream (F) from the second tower is passed into the final product tower (D3), where high-purity DMS is obtained as an overhead stream, and a minor amount of dimethyl disulfide (DMDS) is obtained as a heavy-bottoms stream.

Operable conditions for the desired reactions to occur in the reactor (Rl) are the presence of a zeolite catalyst of Type X, Type Y, or Type L, containing less than 10% of an alkali metal (expressed as $Na_2O$), a catalyst bed temperature in the range 250°–450° C., and pressures ranging from atmospheric to 600 psig. The molar ratio of fresh alkanol and fresh $H_2S$ fed to the system may range from a 3 to 1 molar excess of alkanol over $H_2S$ to a 3 to 1 molar excess of $H_2S$ over alkanol. The molar ratios in the combined fresh-plus-recycle feed (A) to the reactor may, of course, be outside this range, and will usually contain a slight molar excess of $H_2S$ over alkanol, and may be as high as 4 or 5 to 1. The feed (A) to reactor also contains about 5–30 moles of an inert gas or mixture of gases per mole of alkanol, to provide sufficient heat removal from the catalyst zone. The inert gas may be nitrogen, methane, ethane, propane, butane, carbon dioxide, or any non-reactive material or mixture of materials that does not adversely affect the desired reactions to produce DMS. The rate at which the alkanol is passed over the zeolite catalyst may range from about 20 to about 300 gram-moles of alkanol per kilogram of catalyst per 24 hours.

The preferred catalysts are the Type Y synthetic zeolites in which the sodium cation has been exchanged with ammonium, and the catalyst has then been calcined at about 500° C. to remove ammonia, producing essentially a protonated Type Y sieve, in which the sodium content (expressed as $Na_2O$) has been reduced below about 3% by weight. Examples of commercially available zeolites of this preferred type are the Linde LZ-Y62, LZ-Y72, and LZ-Y82 molecular sieve catalysts marketed by Union Carbide Corporation.

The preferred catalyst-bed temperatures are in the range 325°–425° C. and the preferred pressures in the reactor are in the range 50–350 psig. The preferred molar ratio of fresh alkanol to $H_2S$ fed into the reaction system is in the range 2.5/1 to 1/2.5, and is most preferably near the stoichiometric ratio of 2/1. The molar ratio of the inert gas, or mixture of gases, used to remove heat from the exothermic reaction, to the alkanol feed, is preferably between about 8 to 1 and 15 to 1. The inert gases are simply recycled in the system and need not be replenished continuously. The preferred rate at which the alkanol is passed over the zeolite catalyst is in the range 50–150 gram-moles of alkanol per kilogram of catalyst per 24 hours. The preferred alkanol and dialkyl sulfide for which this process is to be used, are methanol and DMS, respectively.

EXAMPLES

The following examples are intended to illustrate the process of this invention and to demonstrate the advantage of the zeolite catalysts. In these examples, the use of a preferred synthetic zeolite catalyst, Union Carbide's LZ-Y62 (Example 1), is compared with the use of a conventional dehydrating catalyst, Alcoa's Grade F-1 activated alumina (Example 2), for the preparation of DMS from methanol and $H_2S$. A synthetic mixture corresponding to the composition of the fresh-plus-recycle feed to the reactor (point A in FLOW DIAGRAM 1) is passed continuously over the catalyst, and the composition of the crude product (point B in FLOW DIAGRAM 1) is determined by gas chromatographic (GC) analyses. The material balances across the reactor, and the single-pass conversions to DMS are calculated from the GC data for each catalyst.

EXAMPLE 1

The catalyst in the reactor is Union Carbide's Linde LZ-Y62 molecular sieve, 1/8" extrudate, which is manufactured by ammonium-exchanging a conventional (sodium) Type Y sieve and calcining it to remove ammonia and produce essentially a protonated Type Y sieve.

Methanol and $H_2S$ are reacted to produce DMS. Methane and carbon dioxide are used as the inert, heat-removing diluents. To simulate a fresh-plus-recyclefeed mixture (A in FLOW DIAGRAM 1), we pumped methanol and methyl mercaptan separately as liquids and metered $H_2S$, $CO_2$ and $CH_4$ separately as gases, at appropriate rates to provide a continuous $CH_3OH/H_2S/CH_4/CO_2/CH_3SH$ mixture in the approximate desired molar ratio 1/2.7/6.7/2.2/11.2.

The above mixture was passed into an electrically-heated preheater maintained at 240°±5° C. to vaporize all materials and then into an electrically-heated, fixed-bed, 316 stainless steel, catalytic reactor maintained at 370°±5° C. The exit stream (B in FLOW DIAGRAM 1) was passed as a vapor by means of electrically-traced stainless steel tubing through a back-pressure control-release valve and directly into the heated gas-sampling device of a gas chromatograph for analysis. The pressure in the reactor system was maintained at 120 psig, and the methanol space velocity was maintained at about 73 gram-moles of $CH_3OH$ per kilogram of catalyst per 24-hour day.

Six experimental, continuous, runs of approximately two-hours duration each were made over about 30 hours of operation. The reaction conditions and product stream GC analyses for each run are given in Table 1.

From the averaged GC analytical data shown at the bottom of Table 1, we calculated a material balance across the reactor, based on 100 lbs total input. The material balance figures are shown in Table 2 and compared with the analogous average material balance values obtained with alumina catalyst (Example 2).

For the Linde LZ-Y62 zeolite catalyst, Table 2 shows that 3.63 lbs (0.11 lb-mols) of methanol and 59.49 lbs (1.24 lb-mols) of methyl mercaptan will produce 23.68 lbs (0.38 lb-mols) of DMS in a single-pass. The amount of DMS theoretically possible is 42.25 lbs (0.68 lb-mols). The single-pass conversion of $CH_3OH$ and $CH_3SH$ combined to DMS is thus: $0.38/0.68 \times 100\% = 56.0\%$.

EXAMPLE 2

Example 1 is repeated, except that the zeolite catalyst is replaced by Alcoa's Grade F-1 activated alumina (8×14 mesh). The material balance across the reactor, based on the average GC analysis of the crude product (B in FLOW DIAGRAM 1) in five two-hour runs, was calculated in the same manner as in Example 1. The results are compared with the zeolite catalyst results of Example 1 in Table 2.

Table 2 shows that with alumina catalyst, 4.05 lbs (0.13 lb-mols) of methanol and 63.90 lbs (1.33 lb-mols) of methyl mercaptan will produce 11.83 lbs (0.19 lb-mols) of DMS in a single pass. The amount of DMS theoretically possible is 45.35 lbs (0.73 lb-mols). The single-pass conversion of $CH_3OH$ and $CH_3SH$ combined to DMS is thus only: $0.19/0.73 \times 100\% = 26.0\%$.

The zeolite catalyst of Example 1 (56% conversion-per-pass) is thus more than twice as efficient as the conventional dehydration catalyst, alumina, of Example 2 (26% conversion-per-pass) for converting methanol and $H_2S$ to DMS in this process. Its advantage over the conventional catalyst appears to be its greater efficiency for converting methyl mercaptan, an intermediate which is recycled in this process, to DMS, according to the equation $2CH_3SH \rightarrow CH_3SCH_3 + H_2S$.

In a similar manner, ethanol and $H_2S$ may be reacted to produce diethyl sulfide, isopropanol and $H_2S$ may be reacted to produce di-isopropyl sulfide; tertiary-butanol may be reacted with $H_2S$ to produce di-tertiary-butyl sulfide; and octanol-1 may be reacted with $H_2S$ to produce di-n-octyl sulfide.

TABLE 1
DMS PROCESS
ZEOLITE CATALYST (Example 1)

| | REACTION CONDITIONS | | | | CRUDE PRODUCT ANALYSIS GAS CHROMATOGRAPH - WEIGHT % | | | | | | | | |
|---|---|---|---|---|---|---|---|---|---|---|---|---|---|
| RUN NUMBER | $CH_3OH$ Mole Velocity (1) | Molar Ratio $CH_3OH/H_2S/CO_2/CH_4/CH_3SH$ | Catalyst Temp. °C. | Pressure psig | $CH_4$ | $CO_2$ | $H_2O$ (2) | $H_2S$ | COS | $CH_3OH$ | $CH_3SH$ | DMS | DMDS |
| 1 | 63 | 1/3.4/3.0/8.5/12.3 | 365 | 120 | 10.30 | 12.36 | (1.79) | 28.79 | 1.08 | 0.21 | 19.75 | 27.46 | Tr. |
| 2 | 75 | 1/2.6/2.5/7.4/11.1 | 372 | 120 | 11.77 | 13.64 | (2.05) | 29.98 | 1.06 | 0.12 | 19.27 | 23.96 | 0.12 |
| 3 | 65 | 1/2.9/2.9/8.2/13.2 | 369 | 120 | 7.04 | 7.85 | (1.77) | 21.64 | 0.84 | 0.11 | 35.03 | 26.67 | 0.78 |
| 4 | 72 | 1/2.7/2.6/7.8/11.8 | 372 | 120 | 11.57 | 6.97 | (1.93) | 26.05 | 0.66 | 0.26 | 21.16 | 32.86 | 0.38 |
| 5 | 91 | 1/2/2.1/5.9/9.8 | 380 | 120 | 13.08 | 16.62 | (2.38) | 34.91 | 1.61 | 0.25 | 16.32 | 17.13 | Tr. |
| 6 | 71 | 1/3.0/2.6/7.5/8.6 | 375 | 120 | 12.68 | 10.72 | (2.31) | 26.87 | 3.94 | Tr. | 27.80 | 16.62 | 1.30 |
| Avg. | 73 | 1/2.8/2.6/7.6/11.1 | 372 | 120 | 11.07 | 11.36 | (2.04) | 28.04 | 1.53 | 0.16 | 23.22 | 24.12 | 0.43 |

(1) Mole velocity = gram-moles/kilogram catalyst/24-hr. day
(2) Theoretical $H_2O$; not determined by GC.

TABLE 2
DMS PROCESS
ZEOLITE VERSUS ALUMINA CATALYST

| MATERIAL 100 lb. BASIS | EXAMPLE 1 ZEOLITE CATALYST | | EXAMPLE 2 ALUMINA CATALYST | |
|---|---|---|---|---|
| | INPUT | OUTPUT | INPUT | OUTPUT |
| $CH_4$ | 13.54 | 10.86 | 12.37 | 14.25 |
| $CO_2$ | 12.81 | 11.14 | 11.33 | 11.00 |
| $H_2O$ | — | 1.95 | — | 2.25 |
| $H_2S$ | 10.54 | 27.59 | 10.73 | 19.22 |
| COS | — | 1.50 | — | 0.33 |
| $CH_3OH$ | 3.63 | 0.16 | 4.05 | 0.04 |
| $CH_3SH$ | 59.49 | 22.79 | 63.90 | 42.75 |
| DMS | — | 23.68 | — | 11.83 |
| DMDS | — | 0.42 | — | — |

We claim:

1. A continuous vapor-phase process for preparing $C_1$–$C_{12}$ dialkyl sulfide that comprises reacting a $C_1$–$C_{12}$ alkanol and hydrogen sulfide at elevated temperature in the presence of a zeolite catalyst having pore openings in the range of from about 7 to about 10 Angstroms, said zeolite catalyst being Type X, Type Y or Type L and containing less than 10% by weight alkali metal, expressed as $Na_2O$.

2. The process of claim 1, wherein the crude reaction product consists of a mixture of a $C_1$ to $C_{12}$ mercaptan and the corresponding $C_1$ to $C_{12}$ dialkyl sulfide, and the mercaptan is separated and recycled over the zeolite catalyst to convert it to additional $C_1$ to $C_{12}$ dialkyl sulfide.

3. The process of claim 2, wherein the catalyst temperature is in the range 250°–450° C.

4. The process of claim 2, wherein the pressure in the reaction zone ranges from atmospheric to 600 psig.

5. The process of claim 2, wherein the molar ratio of alkanol to hydrogen sulfide supplied to the reaction system ranges from 3:1 to 1:3.

6. The process of claim 2, wherein the rate at which the alkanol is passed over the catalyst ranges from 20 to 300 gram-moles of alkanol per kilogram of catalyst per 24 hours.

7. The process of claim 2, wherein an inert gas is continuously recycled through the reaction zone to remove heat from the exothermic reaction.

8. The process of claim 2, wherein the alkali metal content of the zeolite catalyst has been reduced below 10% by exchanging the alkali metal ions with protons or catalytically active cations.

9. The process of claim 2, wherein the alkali metal has been reduced below 10% by exchanging the alkali metal ions with ammonium ions and thereafter the zeolite is calcined to remove at least a major portion of the ammonia.

10. The process of claim 2, wherein the alkanol is methanol and the dialkyl sulfide is dimethyl sulfide.

11. The process of claim 10, wherein the alkali metal content, expressed as $Na_2O$, is below 3% by weight.

12. The process of claim 11, wherein the catalyst temperature is in the range 325°–425° C. and the pressure in the reaction zone is in the range of 50–300 psig.

13. The process of claim 11, wherein the methanol is passed over the zeolite catalyst at a rate in the range of 50–150 gram-moles per kilogram of catalyst per 24 hours, and the molar ratio of methanol to hydrogen sulfide supplied to the reaction system is in the range of 2.5:1 to 1:2.5.

14. The process of claim 11, wherein the intermediate methyl mercaptan in the crude product is separated and recycled to the reactor containing the zeolite catalyst.

15. The process of claim 11, wherein an inert gas or mixture of gases selected from the class consisting of nitrogen, carbon dioxide, and a hydrocarbon, is constantly recycled through the reaction zone in sufficient quantity to remove the excess heat from the reaction zone to maintain the desired catalyst bed temperature.

16. The process of claim 15, wherein methanol and hydrogen sulfide are continuously supplied to the reaction system in a molar ratio of about 2:1, the intermediate methyl mercaptan is continuously separated from the crude reaction product and recycled to the reaction zone, and the remaining crude product is continuously distilled to provide dimethyl sulfide having a purity of at least 99.5%.

* * * * *